United States Patent
Shaer et al.

(10) Patent No.: US 11,360,327 B1
(45) Date of Patent: Jun. 14, 2022

(54) SCLERAL LENS WITH FENESTRATION AND POCKETS

(71) Applicant: FITLENS LTD., Nesher (IL)

(72) Inventors: Soheil Shaer, Nesher (IL); Claes Feinbaum, Nesher (IL); Yujing Bai, Nesher (IL)

(73) Assignee: FITLENS LTD., Nesher (IL)

( * ) Notice: Subject to any disclaimer, the term of this patent is extended or adjusted under 35 U.S.C. 154(b) by 0 days.

(21) Appl. No.: 17/357,405

(22) Filed: Jun. 24, 2021

(30) Foreign Application Priority Data

Dec. 31, 2020 (CN) .......................... 202011637758.8

(51) Int. Cl.
G02C 7/04 (2006.01)
A61F 2/14 (2006.01)

(52) U.S. Cl.
CPC ............ *G02C 7/049* (2013.01); *A61F 2/1451* (2015.04); *A61F 2/15* (2015.04); *G02C 7/04* (2013.01)

(58) Field of Classification Search
CPC . G02C 7/04; G02C 7/02; G02C 7/047; G02C 7/049; A61F 2/15
USPC ........................................ 351/159.04, 159.02
See application file for complete search history.

(56) References Cited

U.S. PATENT DOCUMENTS

| | | | | |
|---|---|---|---|---|
| RE29,229 E | * | 5/1977 | Girard ....................... | G02C 7/04 351/159.01 |
| 5,347,326 A | * | 9/1994 | Volk ....................... | A61B 3/125 351/159.02 |
| 7,695,135 B1 | | 4/2010 | Rosenthal | |
| 8,087,777 B2 | | 1/2012 | Rosenthal | |
| 10,423,010 B2 | | 9/2019 | Otts et al. | |
| 2004/0061828 A1 | * | 4/2004 | Newman ................ | G02C 7/021 351/159.03 |
| 2006/0290883 A1 | * | 12/2006 | Rosenthal .............. | G02C 7/047 351/159.12 |
| 2010/0118262 A1 | | 5/2010 | Rosenthal | |
| 2013/0293832 A1 | | 11/2013 | de Juan, Jr. et al. | |
| 2015/0055081 A1 | * | 2/2015 | de Juan, Jr. ............ | G02C 7/049 351/159.04 |

(Continued)

FOREIGN PATENT DOCUMENTS

WO WO 2015/116559 6/2015

OTHER PUBLICATIONS

Fadel, et al.; "Fenestrated Scleral Lenses: Back to the Origins? Review of Their Benefits and Fitting Techniques;" *Optom Vis. Sci.* 2020; vol. 97(9).

(Continued)

*Primary Examiner* — Jordan M Schwartz
(74) *Attorney, Agent, or Firm* — Haynes and Boone, LLP

(57) ABSTRACT

The present invention provides a scleral lens with a fenestration and pockets. One fenestration or a plurality of annularly-distributed fenestrations are provided in an optic zone of the scleral lens; and two or more pockets are provided in a pocket annular zone on a posterior surface of the optic zone. The pockets are configured to trap gas bubbles near the fenestration, where the fenestration is located radially outward from the pocket annular zone and not located in a transition zone of the scleral lens, and the transition zone is configured to be located above the limbus of the eyeball during wearing of the scleral lens. The lens of the present invention will not be adsorbed to the cornea, and can be worn comfortably and maintain clear visual acuity for up to 12 hours.

17 Claims, 4 Drawing Sheets

(56) References Cited

U.S. PATENT DOCUMENTS

| | | | |
|---|---|---|---|
| 2015/0077701 A1* | 3/2015 | de Juan, Jr. | G02C 7/022 351/159.04 |
| 2019/0353930 A1 | 11/2019 | De Juan, Jr. et al. | |
| 2020/0166777 A1* | 5/2020 | Rafaeli | G02C 7/049 |
| 2020/0264450 A1 | 8/2020 | De Juan, Jr. et al. | |

OTHER PUBLICATIONS

Extended European Search Report dated Jan. 18, 2022, from corresponding Application No. EP 21 18 1640, 3 pages.

* cited by examiner

SCLERAL LENS WITH FENESTRATION AND POCKETS

CROSS-REFERENCE TO RELATED APPLICATION

This application claims priority to Chinese Patent Application No. 202011637758.8, filed on Dec. 31, 2021, the contents of which is hereby incorporated herein in its entirety by express reference thereto.

TECHNICAL FIELD

The present invention relates to the field of technologies in ophthalmology and optometry, and in particular, to a scleral lens with a fenestration and pockets.

BACKGROUND

Contact lenses include corneal contact lenses and scleral lenses. Scleral lenses are large-diameter rigid lenses covering the sclera and the corresponding conjunctiva. Their diameter may range from 14 mm to 25 mm. The scleral lenses may be further subdivided into mini scleral lenses (with a lens diameter ranging from 14 mm to 18 mm) and full scleral lenses (with a lens diameter ranging from 18 mm to 25 mm). A scleral lens generally includes three zones: (1) an optic zone, which spans the cornea but does not touch the cornea and can be used to correct vision if necessary; (2) a transition zone, which connects the optic zone and a landing zone and is located in the limbus zone; and (3) the landing zone (haptic zone), which is used to support the lens on the eyeball, and whose curvature needs to be as consistent as possible with a scleral curvature.

There is a clearance (corneal clearance) between an inner surface of the scleral lens and an anterior surface of the cornea, so that the scleral lens does not directly touch the cornea. Therefore, the scleral lens is especially suitable for patients with irregular cornea or corneal diseases such as keratoconus or marginal corneal degeneration. The scleral lens is designed to bulge in the middle to form a vault. The vault ensures the clearance between the lens and the cornea, which can be used as an effective reservoir for fluid. The fluid can protect the cornea and even help the cornea heal. Therefore, the scleral lens is also applicable to other ocular surface diseases such as Stevens-Johnson syndrome, keratoconjunctivitis sicca, graft rejection, and ocular cicatricial pemphigoid.

Keratoconjunctivitis sicca, also known as xerophthalmia, dry eye syndrome, or the like, is currently the most common ocular surface disease that affects vision and quality of life. Most patients with keratoconjunctivitis sicca may have eye discomfort and even anxiety, depression, and the like. In extreme cases, keratoconjunctivitis sicca can even lead to blindness.

Keratoconjunctivitis sicca is a chronic ophthalmic disease caused by a variety of factors, which are usually unusual quality, amount, and dynamics of tears produced by the patient. The most common treatment is to use an artificial tear supplement to provide extra moisture and lubrication to the surface of the cornea. With its capability of providing a fluid reservoir located on the cornea, the scleral lens provides a good alternative solution for resolving the problem of keratoconjunctivitis sicca.

However, hypoxia is a major problem that the scleral lens needs to solve. Unlike any other body surface tissues of the human body, the cornea obtains oxygen by directly extracting oxygen from the surrounding air rather than from the blood circulation, and when wearing a closed scleral lens, there is almost no tear exchange on the cornea. Therefore, the oxygen contained in the fluid in the corneal clearance is crucial. Although modern high-oxygen permeable materials mostly resolve this problem, due to the absence of tear exchange, the closed scleral lens still has the problem of fogging (veiling or midday fogging) caused by accumulation of metabolites under the lens.

Fenestrated scleral lenses have been proposed to resolve this problem. The fenestration is to bore a small hole in the scleral lens to improve the tear exchange under the lens or provide more available oxygen through the lens. However, such simple fenestration is prone to introduce gas bubbles between the cornea and the lens, which affects visual quality. Fadel et al. (Fadel et al. Fenestrated Scleral Lenses: Back to the Origins? Review of Their Benefits and Fitting Techniques, Optom Vis Sci 2020; Vol 97(9)) suggested that the fenestration should be positioned above the limbus zone so that the gas bubbles were principally retained in the limbus zone of the cornea without affecting vision.

Another problem with the scleral lens is adhesion of the scleral lens and the cornea due to filling of mucin accumulating over time between the cornea and the lens. Still another problem is that the fluid between the scleral lens and the cornea is squeezed out during blinking. If this part of the fluid cannot be replaced in time, the lens would be adsorbed to the eyeball over time, which is dangerous to the eye.

Various designs have been proposed to resolve the above-mentioned problems.

U.S. Pat. No. 7,695,135B1 discloses a scleral lens. A scleral portion of the scleral lens includes one or more channels extending radially from an inner rim to an outside rim of the scleral portion, and the outside rim of the scleral portion defines a scallop where the channel intersects the outside rim of the scleral portion. This patent also discloses a scleral lens including a channel circumscribing the entire optic portion of the scleral lens, and the channel defines at least one fenestration.

U.S. Pat. No. 8,087,777B2 discloses a scleral lens including microchambers formed in a posterior surface of an optic portion of the scleral lens, where the microchambers are configured to increase oxygen permeability of the lens.

SUMMARY

In view of this, the primary purpose of the present invention is to provide a different scleral lens design, to effectively maintain ecological circulation between fluid in a corneal clearance and fluid outside a lens, not only providing continuous and sufficient oxygen to the cornea, but also promoting discharge of gas bubbles and metabolites under the lens. The lens of the present invention will not be adsorbed to the cornea, and can be worn comfortably and maintain clear visual acuity for up to 12 hours.

To achieve the above-mentioned purpose, the present invention provides a scleral lens with a fenestration and pockets. One fenestration or a plurality of annularly-distributed fenestrations are provided in an optic zone of the scleral lens; and two or more pockets are provided in a pocket annular zone on a posterior surface of the optic zone. The pockets are configured to trap gas bubbles near the fenestration, where the fenestration is located radially outward from the pocket annular zone and not located in a transition zone of the scleral lens, and the transition zone is configured to be located above the limbus of the eyeball during wearing of the scleral lens.

In some embodiments, the distance from the geometric center of the fenestration to the geometric center of the scleral lens is 4.0 mm to 7.0 mm, for example, 4.5 mm to 6.5 mm, 4.6 mm to 6.0 mm, or 5.0 mm to 5.5 mm, preferably 5.2 mm to 5.3 mm.

In some embodiments, the optic zone is provided with a maximum of 24 fenestrations, preferably an even number of fenestrations, and/or the number of pockets in the pocket annular zone is at least 2 times, 3 times, 4 times, 5 times, 6 times, 7 times, or more times the number of fenestrations.

In some embodiments, the plurality of annularly-distributed fenestrations are evenly distributed annularly.

In some embodiments, the pockets are evenly distributed annularly in the pocket annular zone, or concentrated near the fenestration(s), provided that the number of pockets near each fenestration is sufficient to trap gas bubbles entering through the fenestration.

In some embodiments, the pocket has an opening in the posterior surface of the optic zone and the opening takes the shape of a circle, ellipse, oval, rectangle, rhombus, or regular polygon; and/or the horizontal cross section of the fenestration takes the shape of a circle, ellipse, oval, rectangle, rhombus, or regular polygon.

In some embodiments, the depth d of the pocket is 0.05 mm to 0.3 mm and the opening has a maximum dimension t ranging from 0.2 mm to 1.0 mm, where t>d, preferably t≥2d, more preferably t≥2.5d, and most preferably, t≥3d; and/or the horizontal cross-section of the fenestration has a maximum dimension ranging from 0.2 mm to 1.0 mm.

In some embodiments, the plurality of annularly-distributed fenestrations have the same or different sizes; and/or the two or more pockets have the same or different sizes.

In some embodiments, the diameter of the inner ring of the pocket annular zone ranges from 5.0 mm to 13.5 mm.

In some embodiments, a total diameter of the scleral lens is 14.0 mm to 25.0 mm, preferably 14.0 mm to 18.0 mm.

In some embodiments, the optic zone has diopter.

BRIEF DESCRIPTION OF DRAWINGS

For the purpose of illustration and not limitation, the present invention is described below with preferred embodiments of the present invention, particularly with reference to the accompanying drawings, in which.

DETAILED DESCRIPTION

Figure 1:
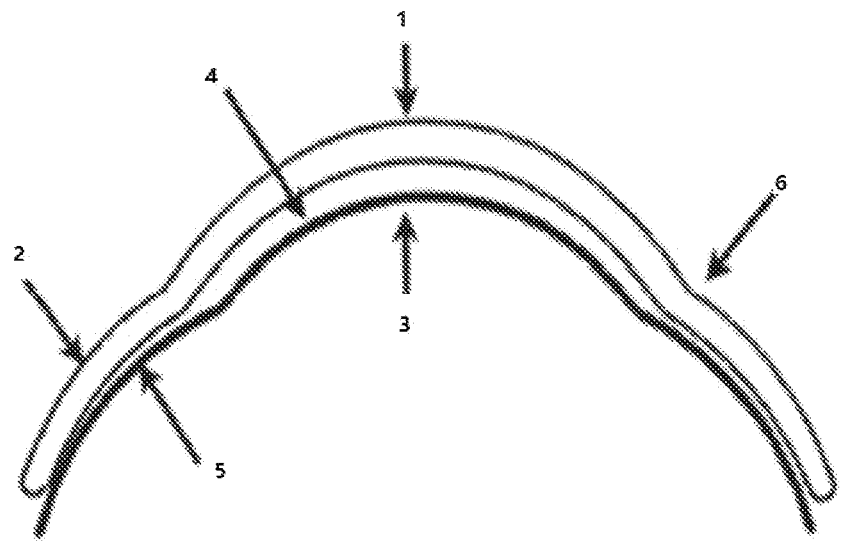
FIG. 1 is a schematic cross-sectional view of a conventional scleral lens.

The following further describes this application in detail with reference to the accompanying drawings and embodiments. It should be understood that, for simplicity and clarity of the illustration, the elements shown in the drawings are not necessarily drawn to scale, and the features presented in each embodiment can be combined with the features presented in other embodiments. Reference signs are repeated across the accompanying drawings to indicate the same or similar elements. It can be understood that the specific embodiments described herein are only used to explain related content, but not to limit the application.

The present invention provides a scleral lens with a fenestration and pockets. The scleral lens does not touch the cornea, and therefore is not easy to be adhered to the cornea and is not likely to be absorbed onto the cornea. The scleral lens provides excellent oxygen permeability and moisture retention, and allows delivery of required fluid from the outside of the lens to the eyeball during wearing of the lens, and therefore is especially suitable for patients with keratoconjunctivitis sicca, persistent corneal epithelial injury, irregular cornea, spherical cornea, keratoconus, or pellucid marginal corneal degeneration, and patients after ophthalmic surgery (for example, transplantation, keratoplasty, photorefractive keratectomy (PRK), and laser in situ keratomileusis (LASIK)).

FIG. 1 is a schematic cross-sectional view of a conventional scleral lens. The scleral lens includes an optic zone 1 and a landing zone 2. The posterior surface of the optic zone is configured to be located above cornea 3 of an eyeball, spaced apart from the anterior surface of the cornea of the eyeball, and not in contact with the cornea of the eyeball, thereby forming a corneal clearance 4. The posterior surface of the landing zone is configured to land at conjunctiva 5 corresponding to a scleral surface of the eyeball. The optic zone 1 and the landing zone 2 are connected by a transition zone 6.

Figure 2:
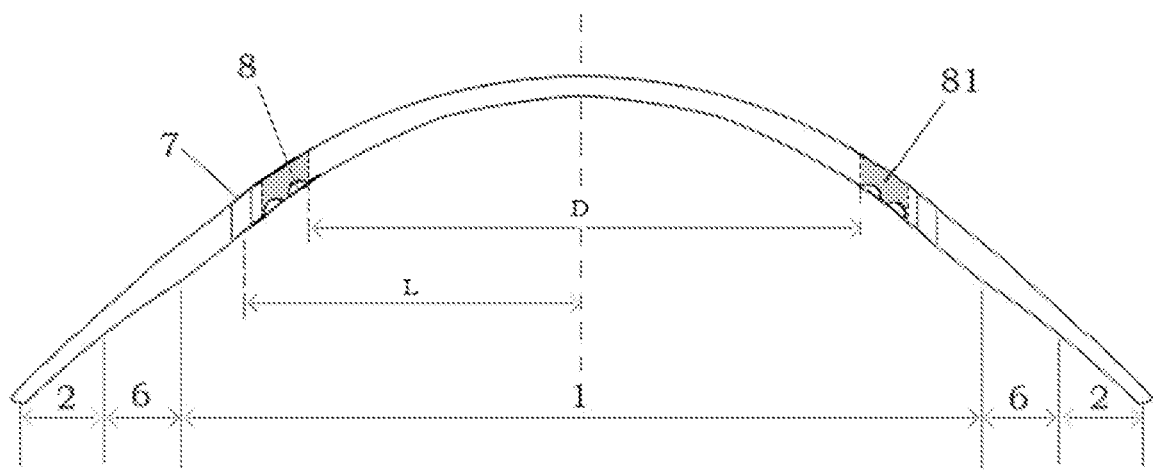
FIG. 2 is a cross-sectional view of a scleral lens according to an embodiment of the present invention.

FIG. 2 is a cross-sectional view of a scleral lens according to an embodiment of the present invention. The scleral lens includes an optic zone 1, a transition zone 6, and a landing zone 2. During wearing of the lens, the anterior surface of the optic zone 1 faces away from the eyeball, and the posterior surface of the optic zone 1 faces toward the anterior surface of the cornea of the eyeball; the transition zone 6 is located above the limbus of the eyeball; and the landing zone 2 is in contact with the conjunctiva on the scleral surface. The optic zone 1 is provided with a fenestration 7 penetrating the anterior and posterior surfaces of the optic zone 1 and pockets 8 in the posterior surface of the optic zone 1. The pockets 8 are located in a pocket annular zone 81 (the zone marked gray in the figure), and located inward from the fenestration 7, meaning the pockets 8 are closer to the center of the lens. The distance from the geometric center of the fenestration 7 to the geometric center of the scleral lens is L. The diameter of the inner ring of the pocket annular zone is D, and D is 2 times the closest distance from the opening of a pocket closest to the center of the lens in the posterior surface of the lens to the center of the lens. Similarly, the diameter of the outer ring of the pocket annular zone is 2 times the farthest distance from the opening of a pocket farthest from the center of the lens in the posterior surface of the lens to the center of the lens.

In embodiments of the present invention, the fenestration and the pockets are not arranged in the transition zone 6, meaning not being arranged in the limbus zone. According to Fadel et al., arranging the fenestration in the limbus zone helps retain gas bubbles produced principally within the limbus zone without affecting vision. However, because the clearance between the lens and the eyeball is small (generally 50 μm to 100 μm) in this zone, which is not conducive to fluid exchange expected from the present invention, the fenestration is arranged in a zone other than the limbus zone in various embodiments of the present invention.

In various embodiments of the present invention, the distance L from the geometric center of the fenestration to the geometric center of the scleral lens is 4.0 mm to 7.0 mm, for example, 4.5 mm to 6.5 mm, 4.6 mm to 6.0 mm, or 5.0 mm to 5.5 mm, preferably 5.2 mm to 5.3 mm.

The fenestration in the present invention penetrates the anterior and posterior surfaces of the scleral lens, allowing fluid communication between the inner and outer sides of the scleral lens, allowing tears or eye drops to enter the fluid storage zone (corneal clearance) between the lens and the cornea during wearing, and allowing metabolites generated on the ocular surface under the lens to be discharged in time. Because a small aperture cannot guarantee a smooth flow of fluid due to the action of liquid tension, the fenestration in the present invention preferably has a larger size, for example, a maximum horizontal cross-sectional dimension greater than 0.2 mm, for example, ranging from 0.2 mm to 1.0 mm, from 0.3 mm to 0.9 mm, from 0.4 mm to 0.8 mm, from 0.5 mm to 0.7 mm, or from 0.55 mm to 0.6 mm, for example, being 0.25 mm, 0.35 mm, 0.45 mm, 0.65 mm, 0.75 mm, 0.85 mm, 0.95 mm, or 0.99 mm, and more preferably, being, for example, 0.46 mm, 0.47 mm, 0.48 mm, 0.49 mm, 0.501 mm, 0.51 mm, 0.52 mm, 0.53 mm, or 0.54 mm. In some embodiments, the plurality of fenestrations in the lens have a same size, to be specific, have the same contour and approximately the same maximum horizontal cross-sectional dimension. In still some other embodiments, the plurality of fenestrations in the lens have different sizes.

In the various embodiments of the present invention, the optic zone is provided with a maximum of 24 fenestrations, preferably an even number of fenestrations, for example, 24, 22, 20, 18, 16, 14, 12, 10, 8, 6, 4, 2 fenestrations. Certainly, an odd number of fenestrations, for example 1 or 3, is also feasible.

A scleral lens with a large-size fenestration is prone to introduce gas bubbles between the cornea and the lens during wearing of the lens, which affects vision correction. The present invention successfully resolves this problem by providing a pocket annular zone between the fenestration and the center of the lens. Two or more pockets are arranged in the pocket annular zone for trapping gas bubbles near the fenestration, and the pockets are arranged on the posterior surface of the optic zone without penetrating the anterior surface of the optic zone. To achieve this purpose, the present invention requires that the number of pockets in the pocket annular zone be at least 2 times, for example, 3 times, 4 times, 5 times, 6 times, 7 times, or more times, the number of fenestrations. For example, when the scleral lens has one fenestration, at least two pockets are provided in the pocket annular zone. In this case, due to the small number of pockets, preferably the pockets are concentrated near the fenestration (as shown in FIG. 3), so as to effectively trap gas bubbles that may be introduced through the fenestration.

It should be understood that because objectively speaking, the pockets themselves can reduce paths required for the gas outside the lens to enter the lens, and increase the oxygen permeability of the lens, those skilled in the art can arrange more pockets in the scleral lens of the present invention than required for trapping gas bubbles, so as to gain additional benefits of improving oxygen permeability of the lens. The maximum number of pockets is not limited, provided that the number of pockets and their depth do not damage structural integrity of the scleral lens. It is believed that, the greater the number of the pockets, the better management of the gas bubbles in the fluid storage zone, and the better the fluid retention, and the better the oxygen permeability of the scleral lens. However, for the sake of simplicity in design and manufacture, in a preferred embodiment, the number of pockets does not exceed 100, for example, less than 90, 80, 70, or 60.

Figure 4:
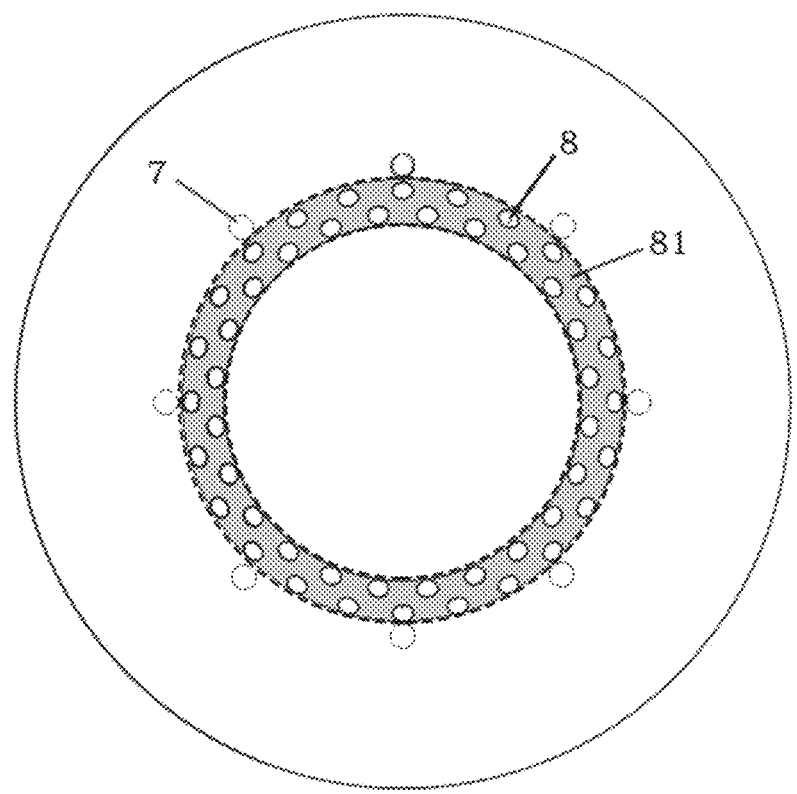
FIG. 4 is a bottom view of a scleral lens according to another embodiment of the present invention.

In some other embodiments, the plurality of fenestrations 7 and the plurality of pockets 8 are evenly distributed annularly. Being evenly distributed annularly means being evenly distributed along one or more rings. FIG. 4 shows eight fenestrations 7 evenly distributed annularly, where 48 pockets 8 are located in a pocket annular zone 81 (a gray zone in the figure) and evenly distributed along two rings. In some other embodiments, a different number of pockets is provided in each ring, for example, fewer pockets being provided along an inner ring. Pockets along different rings are spread out in a staggered manner, so as to provide a tightest-possible bubble trapping net for the radially outwardly located fenestration.

Figure 3:
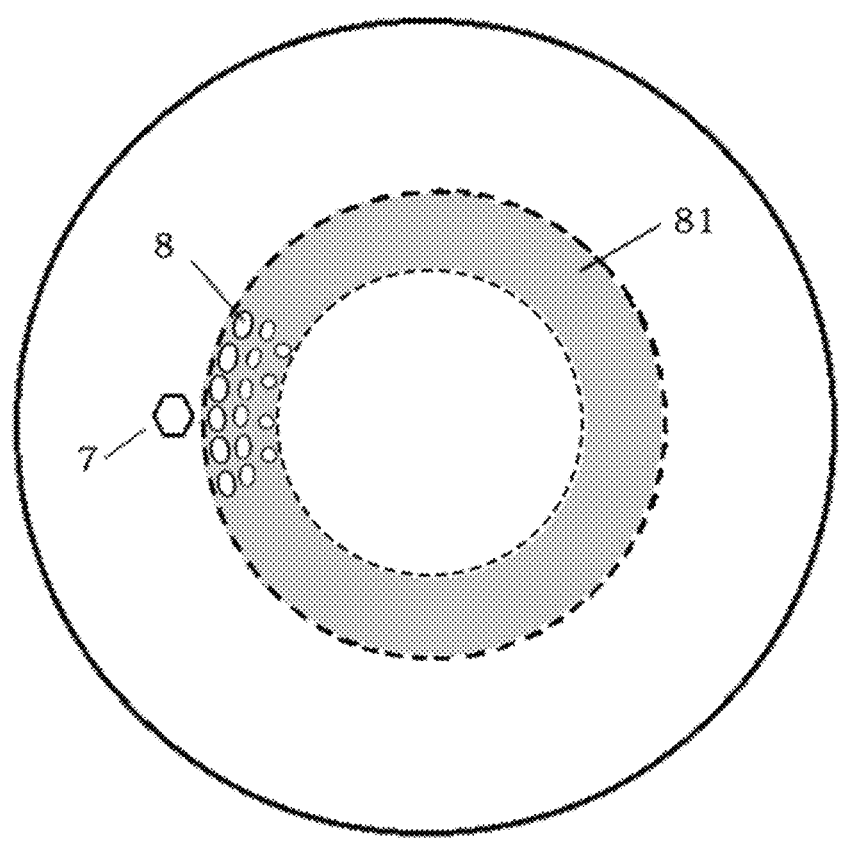
FIG. 3 is a bottom view of a scleral lens according to an embodiment of the present invention.

It should be noted that FIG. 3 and FIG. 4 only show exemplary embodiments of the present invention. In the embodiment, the fenestrations 7 are closely adjacent to the outer ring of the pocket annular zone 81. However, in other exemplary embodiments, the fenestrations 7 and the outer ring of the pocket annular zone 81 may be spaced by a specified distance.

The fenestrations applicable to the present invention may have various horizontal cross-sectional shapes, for example, the shape of a circle, ellipse, oval, rectangle, rhombus, or regular polygon, preferably the shape of a circle, ellipse, or oval. The maximum dimension of the horizontal cross section falls within 0.2 mm to 1.0 mm. The maximum dimension is, for example, the diameter of a circle, the major axis of an ellipse, the largest diagonal of a rhombus, or the like. The maximum dimension of the horizontal cross section gradually becomes larger, gradually smaller, or remains consistent in a direction extending from the anterior surface to the posterior surface of the scleral lens. In conjunction with opening and closing movements of the upper and lower eyelids, this size is sufficient to allow fluid outside the lens (for example, tears and eye drops) to effectively flow into the storage zone between the scleral lens and the eyeball, promoting tear exchange and improving oxygen permeability of the scleral lens.

Similarly, the pockets applicable to the present invention can form openings of various shapes in the posterior surface of the scleral lens, for example, the shape of a circle, ellipse, oval, rectangle, rhombus, or regular polygon. The opening has a maximum dimension t. In some embodiments, t ranges from 0.2 mm to 1.0 mm, from 0.3 mm to 0.9 mm, from 0.4 mm to 0.8 mm, from 0.5 mm to 0.7 mm, or from 0.55 mm to 0.6 mm, for example, being 0.25 mm, 0.35 mm, 0.45 mm, 0.65 mm, 0.75 mm, 0.85 mm, 0.95 mm, or 0.99 mm, and more preferably, being 0.46 mm, 0.47 mm, 0.48 mm, 0.49 mm, 0.501 mm, 0.51 mm, 0.52 mm, 0.53 mm, or 0.54 mm.

Figure 5A:
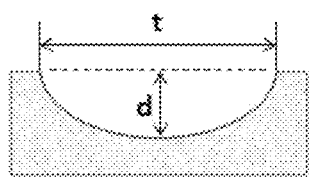
FIG. 5A to FIG. 5C show exemplary configurations of a pocket applicable to the present invention.
Figure 5B:
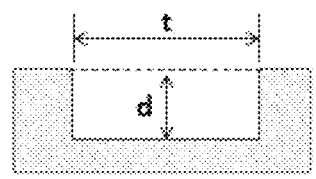
Figure 5C:
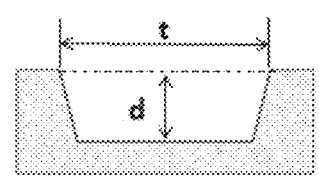

FIG. 5A to FIG. 5C show exemplary configurations of pockets applicable to the present invention. In the design of the present invention, the pockets are configured to capture and trap gas bubbles that may enter the corneal clearance through the fenestration. Therefore, the maximum dimension t of the opening of a pocket is required to be greater than the depth d of the pocket. In some embodiments, $t \geq 2d$. In some embodiments, $t \geq 2.5d$. In some embodiments, $t \geq 3d$. In some embodiments, d ranges from 0.05 mm to 0.3 mm, from 0.1 mm to 0.25 mm, or from 0.15 mm to 0.2 mm, for example, being 0.08 mm, 0.12 mm, 0.16 mm, 0.24 mm, or 0.28 mm.

In some embodiments, the two or more pockets configured in the scleral lens of the present invention have the same size, to be specific, having the same contour and approximately the same maximum dimension t and the same depth d. In some other embodiments, the two or more pockets have different sizes. In still some other embodiments, the size of a pocket near the center of the scleral lens is smaller than the size of a pocket near the outside of the scleral lens (as shown in FIG. 3).

Figure 6:
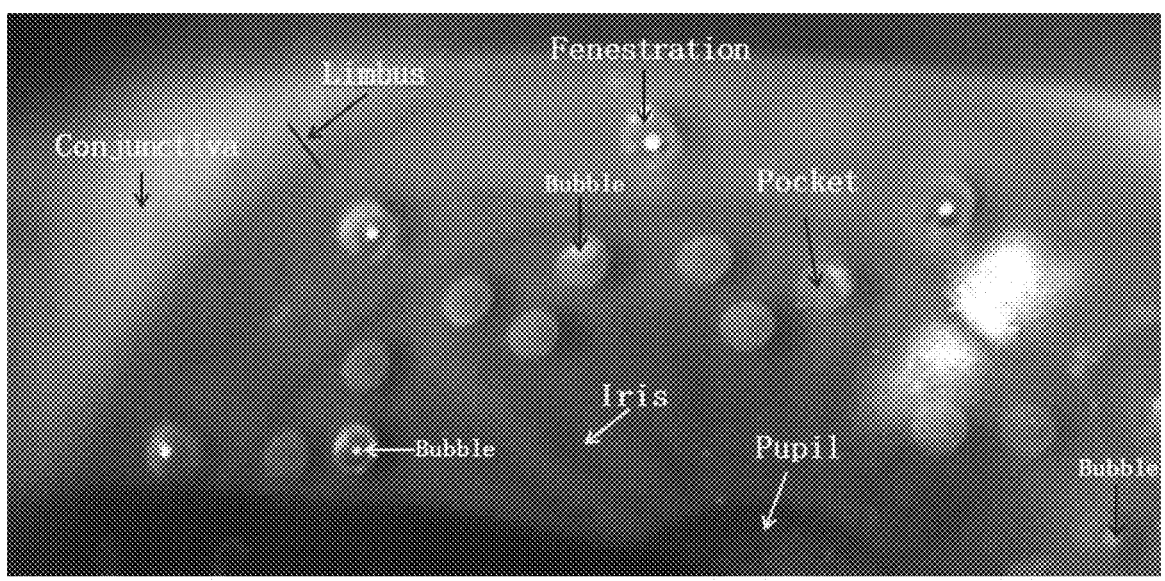
FIG. 6 is a photograph of a scleral lens on an eyeball according to an embodiment of the present invention.

In the scleral lens of the present invention, the pockets are not dedicated to reducing gas bubbles. As is known by those skilled in the art, proper fitting is the key to reducing gas bubbles during wearing of the scleral lens. In the design of the present invention, the pockets are mainly configured for control and management of gas bubbles that may enter the corneal clearance through the fenestration. Therefore, the gas bubbles are controlled to be in the pocket annular zone (as shown in FIG. 6) and cannot enter the pupil zone to affect visual acuity. Based on this, the diameter of the inner ring of the pocket annular zone ranges from 5.0 mm to 13.5 mm, from 6.0 mm to 13.0 mm, from 7.0 mm to 12.0 mm, from 8.0 mm to 11.0 mm, or from 9.0 mm to 10.0 mm. The controlled gas bubbles are not free, so they will not gather to form large gas bubbles and increase the risk of abrasion of the cornea because the air containing the gas bubbles is drier than the fluid in the corneal clearance and may rub the corneal epithelium as if being a solid foreign body.

The design of the pocket and the fenestration in the scleral lens of the present invention provides the scleral lens of the present invention with additional benefits compared to a conventional scleral lens. Therefore, the scleral lens of the present invention is not only suitable for people who are intolerant to small-diameter corneal gas-permeable lenses (contact lenses), and patients with irregular cornea, spherical cornea, keratoconus, pellucid marginal corneal degeneration, or irregular astigmatism, and because the scleral lens can deliver tears or therapeutic/wetting eye drops directly through the fenestration, the scleral lens is also particularly suitable for patients after ophthalmic surgery, such as keratoplasty, PRK, and LASIK, and patients with keratoconjunctivitis sicca. Therefore, other aspects of the present invention further relate to use of the scleral lens in the treatment of the above-mentioned diseases or disorders.

Although specific embodiments have been described herein, many alternatives, modifications, and changes are apparent for those skilled in the art. Those skilled in the art should understand that, depending on design requirements and other factors, various modifications, combinations, subcombinations, and substitutions can be made. Any modification, equivalent replacement, or improvement made without departing from the spirit and principle of the present invention shall fall within the protection scope of the present invention.

What is claimed is:

1. A scleral lens comprising:
   i. an optic zone that extends over the cornea of a wearer's eyeball upon wearing of the scleral lens;
   ii. a landing zone that is configured to land at a conjunctiva corresponding to a scleral surface of the eyeball upon wearing of the scleral lens; and
   iii. a transition zone that connects the optic zone and the landing zone and is configured to be located above a limbus when associated with the eyeball upon wearing of the scleral lens, wherein the optic zone comprises:
      (1) an annular zone in which a plurality of pockets are annularly provided, the annular zone having an inner circumference and an outer circumference and being disposed on a posterior surface of the optic zone; and
      (2) a fenestration located radially outward from the annular zone and not located in the transition zone, and
   wherein the pockets are configured to retain gas bubbles near the fenestration, and the diameter of the inner circumference of the annular zone ranges from 5 mm to 13.5 mm, wherein the number of pockets in the annular zone is at least 2 times more than the number of fenestration(s).

2. The scleral lens according to claim 1, comprising a plurality of fenestrations, wherein the distance from the geometric center of the fenestration to the geometric center of the scleral lens is within the range of 4 mm to 7 mm.

3. The scleral lens according to claim 1, wherein the optic zone is provided with a maximum of 24 fenestrations that are located radially outward from the annular zone and not located in the transition zone.

4. The scleral lens according to claim 3, wherein the fenestrations are evenly distributed in a ring disposed around the annular zone.

5. The scleral lens according to claim 1, wherein the pockets are either evenly distributed annularly in the annular zone, or primarily concentrated in the annular zone near the fenestration.

6. The scleral lens according to claim 1, wherein each pocket has an opening in the posterior surface of the optic zone and the opening takes the shape of a circle, ellipse, oval, rectangle, rhombus, or regular polygon; or the horizontal cross section of the fenestration takes the shape of a circle, ellipse, oval, rectangle, rhombus, or regular polygon; or a combination thereof.

7. The scleral lens according to claim 1, wherein the depth d of at least one pocket is within the range of 0.05 mm to 0.3 mm and the opening of at least one pocket has a maximum dimension t ranging from 0.2 mm to 1.0 mm, and further wherein t>d, or the horizontal cross-section of the fenestration has a maximum dimension ranging from 0.2 mm to 1 mm; or a combination thereof.

8. The scleral lens according to claim 3, wherein the fenestrations have the same size; or the two or more pockets have the same size; or a combination thereof.

9. The scleral lens according to claim 1, wherein a total diameter of the scleral lens is within the range of 14 mm to 25 mm.

10. The scleral lens according to claim 1, wherein the optic zone has a diopter.

11. The scleral lens according to claim 2, wherein the distance from the geometric center of the fenestration to the geometric center of the scleral lens is within the range of 5 to 5.5 mm.

12. The scleral lens according to claim 3, wherein the optic zone is provided with an even number of fenestrations.

13. The scleral lens according to claim 1, wherein the number of pockets in the annular zone is at least 7 times than the number of fenestrations.

14. A scleral lens comprising:
   i. an optic zone that extends over the cornea of a wearer's eyeball upon wearing of the scleral lens;
   ii. a landing zone that is configured to land at a conjunctiva corresponding to a scleral surface of the eyeball upon wearing of the scleral lens; and
   iii. a transition zone that connects the optic zone and the landing zone and is configured to be located above a limbus when associated with the eyeball upon wearing of the scleral lens, wherein the optic zone comprises:
      (1) an annular zone in which a plurality of pockets are annularly provided, the annular zone having an inner circumference and an outer circumference and being disposed on a posterior surface of the optic zone; and
      (2) a fenestration located radially outward from the annular zone and not located in the transition zone, and wherein the pockets are configured to retain gas bubbles near the fenestration, and the diameter of the inner circumference of the annular zone ranges from 5 mm to 13.5 mm, wherein the depth d of at least one pocket is within the range of 0.05 mm to 0.3 mm and the opening of at least one pocket has a maximum dimension t ranging from 0.2 mm to 1.0 mm, and further wherein $t \geq 2d$, or the horizontal cross-section of the fenestration has a maximum dimension ranging from 0.2 mm to 1 mm; or a combination thereof.

15. The scleral lens according to claim 14, wherein $t \geq 3d$.

16. The scleral lens according to claim 9, wherein the total diameter of the scleral lens is within the range of 14 mm to 18 mm.

17. A method of wearing a scleral lens, which comprises applying the scleral lens of claim 1 to an eyeball.

* * * * *